United States Patent [19]
Tu et al.

[11] Patent Number: 6,077,298
[45] Date of Patent: Jun. 20, 2000

[54] EXPANDABLE/RETRACTABLE STENT AND METHODS THEREOF

[76] Inventors: Lily Chen Tu; Hosheng Tu, both of 2151 Palermo, Tustin, Calif. 92782

[21] Appl. No.: 09/253,648

[22] Filed: Feb. 20, 1999

[51] Int. Cl.⁷ ..................................................... A61F 2/00
[52] U.S. Cl. ........................................................ 623/1.19
[58] Field of Search ................................. 623/1, 11, 12, 623/1.19; 606/28, 198

[56] References Cited

U.S. PATENT DOCUMENTS

| | | | |
|---|---|---|---|
| 4,632,842 | 12/1986 | Karwoski et al. | 427/2 |
| 4,718,907 | 1/1988 | Karwoski et al. | 623/12 |
| 4,733,665 | 3/1988 | Palmaz | 128/343 |
| 5,246,451 | 9/1993 | Trescony et al. | 623/1 |
| 5,749,880 | 5/1998 | Banas et al. | 606/198 |
| 5,810,870 | 9/1998 | Myers et al. | 606/198 |
| 5,827,268 | 10/1998 | Laufer | 606/28 |

*Primary Examiner*—Michael J. Milano

[57] ABSTRACT

A retractable intraluminal medical device for treating tissues in a patient, the device comprising an elongate radially expandable/retractable tubular stent having an interior luminal portion and an opposite exterior portion extending along a longitudinal stent axis; a first of the plurality construction materials being a shape-memory Nitinol, the shape-memory Nitinol having a preshape and a shape transition temperature, wherein the shape-memory Nitinol retracts to its preshape and causes the expandable tubular stent to collapse when the shape-memory Nitinol is heated to above the shape transition temperature at a retracted state.

18 Claims, 5 Drawing Sheets

EXPANDABLE/RETRACTABLE STENT AND METHODS THEREOF

FIELD OF THE INVENTION

The present invention generally relates to improved intraluminal medical device and methods for treating tissues. More particularly, the present invention relates to such an expandable and retractable stent for supporting and reinforcing an enlarged vessel having a beneficial advantage of reduction in vessel restenosis, whereas the stent is retractable when it is clinically needed.

BACKGROUND OF THE INVENTION

A stent is a generally longitudinal tubular device formed of biocompatible material, preferably a metallic or a plastic material, which is useful in the treatment of stenosis, strictures or aneurysms in body vessels such as blood vessels. It is well known to employ a stent for the treatment of diseases of various body vessels. The device is implanted either as a "permanent stent" within the vessel to reinforce collapsing, partially occluded, weakened or abnormally dilated sections of the vessel or as a "temporary stent" for providing therapeutic energy treatment to the diseased vessels. A permanent stent may need to be retracted if the stent is not placed at an appropriate site or for other reasons; therefore, it becomes a temporary stent. Stents are typically employed after angioplasty of a blood vessel to prevent restenosis of the diseased vessel. Stents may be useful in other body vessels such as the urological tract and bile duct. The temporary stent is defined in this invention as a stent that is expandable inside a vessel and retractable thereafter from the vessel of a patient.

Stents generally include an open flexible configuration. The stent configuration allows the stent to be configured in a radially compressed state for intraluminal catheter insertion to an appropriate site. Once properly positioned adjacent the damaged vessel, the stent is radially expanded so as to support and reinforce the vessel. Radial expansion of the stent may be accomplished by an inflatable balloon attached to a catheter or the stent may be of the self-expanding type that will radially expand once deployed from the end portion of a delivery catheter. One stent example is U.S. Pat. No. 4,733,665 to Palmaz, which is incorporated herein by reference.

An expanded PTFE (ePTFE) vascular graft is well known to have a substantially non-thrombogenic fluorinated surface. An ePTFE patch is also used for repairing the ruptured blood vessel wall. An ePTFE graft and its process of making are well known to one who is skilled in the art.

U.S. Pat. No. 5,810,870 to Myers et al. discloses a stent covered by an ePTFE to take the advantage of the substantially non-thrombogenic properties of a fluorinated surface, wherein the ePTFE cover exhibits suitable expansion capabilities so as to enable the cover to expand upon expansion of the underlying stent. The ePTFE covered stent exposes the fluorinated ePTFE surface, not the stent surface, to the underlying tissue or the flowing blood stream. Occasionally, the ePTFE cover might shift itself from its associated stent because the ePTFE cover is loosely on the stent. This misalignment phenomenon of an ePTFE cover on a stent becomes a clinical problem when the stent is non-retractably deployed because the ePTFE cover does not firmly adhere to the stent structure. Said ePTFE covered stent also blocks the openness of the stent and does not allow blood to continuously provide nutrient to the tissue behind the implanted stent. Tissue necrosis might occur due to inadequate perfusion, especially for a long ePTFE-covered stent.

U.S. Pat. No. 4,632,842 to Karwoski et al., U.S. Pat. No. 4,718,907 to Karwoski et al., and U.S. Pat. No. 5,246,451 to Trescony et al. disclose one fluorine-containing coating technique for coating fluorine, fluoride, or fluorine-containing compound onto the surface of a substrate to have a very low surface energy and to be essentially non-thrombogenic. However, none of the above-referred patents teaches coating fluorine, fluoride, or fluorine-containing compounds onto a stent that has a very small stent material surface to open surface ratio. Other preferred techniques of depositing fluorine-containing material onto a stent include dipping, dip coating, pasting (or paste coating), and/or sintering processes.

Furthermore, Radiofrequency has been used to provide thermal energy to an "electrode", wherein the electrode is defined as a metallic element that contacts a tissue of a patient, such as a metallic stent in this invention. The radiofrequency energy is delivered from an active "electrode" to a tissue and returns from a dissipating electrode to the radiofrequency generator. The radiofrequency treatment exposes a patient to minimal side effects and risks. Radiofrequency energy, when coupled with a temperature control mechanism, can be supplied precisely to the apparatus-to-tissues contact site to obtain the desired temperature for treating a tissue.

A stent deployed within a vessel, such as a coronary stent, has excellent metal-to-tissue contact surface. It becomes an ideal medium for receiving thermal energy from the ablated tissue to the stent when a stent needs to be collapsed for whatever reasons using a shape-memory Nitinol electrode. RF energy can be applied to a surface fluorinated stent to render the stent less prone to restenosis, too.

Therefore, there is a first need for an improved tubular stent having radially expandable and retractable capabilities for emergency removal when there is a clinical requirement. Furthermore, there is a second clinical need to provide a surface fluorinated retractable stent or a retractable stent having its surface coated by fluorine-containing material while still preserve the openness of the stent configuration, such as a coil stent, a mesh stent, a scaffold stent, a sleeve stent, a porous stent, or a permeable stent.

SUMMARY OF THE INVENTION

In general, it is an object of the present invention to provide an intraluminal medical device comprising a radially expandable and retractable stent for intraluminal medical applications. It is another object to provide a process of making same and method for using same for an expandable and retractable stent. It is a further object of the present invention to provide a thermal system by using an external RF generator for providing RF energy through the expandable stent to cause the stent to collapse, wherein the expandable stent has a shape-memory Nitinol.

In one preferred embodiment, an intraluminal medical device comprises an elongate radially expandable tubular stent having an interior luminal portion and an opposite exterior portion extending along a longitudinal stent axis, the elongate radially expandable tubular stent having an expanded state and a retracted state, wherein the expandable tubular stent comprises a plurality of construction materials. In one embodiment, a first of the plurality of construction materials is a shape-memory Nitinol, the shape-memory Nitinol having a preshape and a shape transition temperature, wherein the shape-memory Nitinol retracts to its preshape and causes the expandable tubular stent to collapse when said shape-memory Nitinol is heated to above the shape transition temperature at the retracted state. The shape transition temperature for the shape-memory Nitinol is preferably between 43° C. and 90° C.

The stent in this invention may include a permanent implantable stent, an implantable grafted stent, or a temporary stent, wherein the temporary stent is defined in this invention as a stent that is expandable inside a vessel and retractable thereafter from the vessel of a patient. The stent configuration may be selected from a group consisting of a coil stent, a memory coil stent, a Nitinol stent, a mesh stent, a scaffold stent, a sleeve stent, a permeable stent, a stent having a temperature sensor, a porous stent made of porous material, a combination of the above, and the like. The stent may be deployed by an inflatable balloon on a catheter, by a self-deployable mechanism after released from a delivery catheter, or by other appropriate means. The elongate radially expandable tubular stent may be a vascular stent, a grafted stent, wherein the grafted stent is a composite device having a stent inside or outside of a graft. The graft may be a vascular graft (also known as vascular prosthesis), such as an ePTFE graft, a biological graft, or a woven graft.

In a preferred embodiment, a second of the plurality of construction materials may be selected from a group consisting of stainless steel, gold, silver, copper, Nitinol, platinum, and an alloy of the mixtures. The elongate radially expandable tubular stent may be selected from a group consisting of a vascular stent, a grafted stent, a coil stent, a mesh stent, a scaffold stent, a sleeve stent, a porous stent made of porous material, and a permeable stent. In a further embodiment, the expandable tubular stent comprises an appropriate quantity of the first of the plurality of construction materials (i.e., shape-memory Nitinol) adapted to cause the expandable tubular stent to collapse when the stent is at a retracted state.

In a still further embodiment, the retractable intraluminal medical device further comprises RF current generating means for generating RF current, wherein the RF current generating means is connected to the radially expandable tubular stent, is adapted for delivering RF current to the radially expandable tubular stent and causes the radially expandable tubular stent to collapse due to its preshape shape-memory. The retractable intraluminal medical device may further comprise temperature sensing means positioned at close proximity of the exterior portion of the expandable tubular stent for measuring temperature, wherein said temperature-sensing means comprises a thermocouple or a thermister measuring probe. The retractable intraluminal medical device may further comprise temperature control means for receiving temperature readings, wherein the temperature readings sensed from the temperature sensing means is relayed to the temperature control means and is adapted to effect the RF current delivery to the expandable tubular stent. The RF current is preferably within the range of 50 to 2,000 kHz.

In one additional embodiment, the exterior surface of the expandable tubular stent of the retractable intraluminal medical device of the present invention has fluorine containing coating. The exterior surface of a stent having fluorine-containing compound is to render the tissue-contacting surface biocompatible. It is well known to one who is skilled in the art that a fluorinated surface has low surface energy and is highly biocompatible and hemocompatible. The "fluorine-containing surface" is synonymous in this invention to "fluorinated surface", which substrate surface is covered or impregnated with fluorine, fluoride, other fluorine-containing compounds, and the like.

In an additional alternate embodiment, the interior luminal surface or an entire surface of the elongate radially expandable tubular stent of the retractable intraluminal medical device of the present invention has fluorine-containing compounds. The interior luminal surface having fluorine-containing coating is to render the fluid contacting surface biocompatible or blood compatible. The fluorine-containing coating and its process may be selected from a group consisting of glow discharge coating, adhesive coating, impregnating coating, compound coating, dip coating, paste coating, and sintering. The dip coating and paste coating on a metallic substrate followed by sintering has been extensively used to coat the frying pans and the like, and is well known to one who is skilled in the art. One class of the fluorine-containing material used in said coating process has a tradename of Teflon® (a tradename of Du Pont Company).

U.S. Pat. No. 4,632,842 to Karwoski et al., U.S. Pat. No. 4,718,907 to Karwoski et al., and U.S. Pat. No. 5,246,451 to Trescony et al. disclose a glow discharge coating technique for coating fluorine-containing compounds onto the surface of a substrate to have a very low surface energy and to be essentially non-thrombogenic. Said patents are incorporated herein by reference. The process for making a surface fluorinated stent includes deposition onto the stent of a fluorine-containing coating by inducing glow discharge progressively along the stent inside a reaction vessel. A polymerizable fluorine-containing gas, such as tetrafluoroethylene and the like, is flown through the stent in the reaction vessel. A radiofrequency field is applied to the gas within the vessel so that a fluorine-containing compound is deposited onto the surface of the stent. In the case of coating one side of the stent, only the surface to be coated is exposed to the glow discharged fluorine-containing gas.

Alternately, a process for making a surface of an intraluminal medical device biocompatible comprises surface treatment means for coating or depositing fluorine or a fluorine-containing material on the surface of the retractable intraluminal medical device. The retractable intraluminal medical device may be an elongate radially expandable tubular stent, an elongate radially expandable tubular grafted stent and the like. The surface treatment means for coating/depositing fluorine or a fluorine-containing material on the surface of the retractable intraluminal medical device may be selected from a group consisting of glow discharge coating, adhesive coating, impregnating coating, compound coating, dip coating, paste coating, and sintering. The treated surface is selected from a group consisting of an interior luminal surface, an exterior surface or an entire surface of the retractable intraluminal medical device. The stent may be made of a porous material to enhancing fluorine deposition or coating into its plurality of micropores, wherein the microporous size is preferably about 100 microns or less.

Briefly, heat is generated by supplying a RF energy source to the retractable intraluminal medical stent, which is comprised of one electrode means in contact with the body tissues. The "electrode means" in this invention is defined to comprise an implantable stent, grafted stent, or a temporary stent capable of contacting the underlying tissue in an appropriate tissue site when the stent is deployed. The RF energy can be applied to the electrode means and consequently to the tissues. A DIP (dispersive indifferent pad) type pad or electrode, that contacts the patient, is connected to the Indifferent Electrode Connector on the RF generator. Therefore, the RF energy delivery becomes effective when a close circuit from a RF generator through a patient and returning to the RF generator is formed. The generator should be grounded to avoid electrical interference. Heat is controlled by the power of the RF energy delivered, the delivery mode, and by the delivery duration. The standard RF energy generator means and its applications through electrode means, to a patient are well known for those who are skilled in the art. The temperature rise on the stent is reflected back from the heated tissue by contacting that stent.

A method for treating an intraluminal tissue of a patient comprises the steps of positioning a retractable intraluminal medical device at an appropriate intraluminal tissue site, wherein the retractable intraluminal medical device comprises an elongate radially expandable tubular stent having an interior luminal portion and an opposite exterior portion extending along a longitudinal stent axis, the elongate radially expandable tubular stent having an expanded state and a retracted state, wherein the expandable tubular stent comprises a plurality of construction materials; and a first of the plurality of construction materials being a shape-memory Nitinol, the shape-memory Nitinol having a preshape and a shape transition temperature, wherein the shape-memory Nitinol retracts to its preshape and causes the expandable tubular stent to collapse when said shape-memory Nitinol is heated to above the shape transition temperature at the retracted state. The method further comprises deploying the radially expandable tubular stent. In an alternate embodiment, the method comprises collapsing the radially expandable tubular stent and retracting the collapsed stent from a body of a patient.

The method for treating an intraluminal tissue of a patient further comprises deploying the radially expandable tubular stent by an inflatable balloon on a catheter. The method further comprises applying RF current to the expandable tubular stent to effect collapsing of the radially expandable tubular stent, wherein the retractable intraluminal medical device further comprises RF current generating means for generating RF current, wherein the RF current generating means is connected to the radially expandable tubular stent and is adapted for delivering RF current to the radially expandable tubular stent. The method further comprises measuring temperature, wherein the retractable intraluminal medical device further comprises temperature sensing means positioned at close proximity of the exterior portion of the expandable tubular stent, and wherein said temperature sensing means comprises a thermocouple or a thermister measuring probe. The method may further comprise relaying measured temperature from the temperature sensing means to a temperature control means, wherein the temperature sensed is adapted to effect the RF current delivery to the expandable tubular stent.

In a further preferred embodiment, a retractable intraluminal medical device comprises an elongate radially expandable tubular stent having an interior luminal portion and an opposite exterior portion extending along a longitudinal stent axis, the elongate radially expandable tubular stent having an expanded state and a retracted state, wherein the expandable tubular stent comprises a first construction material and a second construction material. The first construction material is a shape-memory Nitinol, the shape-memory Nitinol having a preshape and a shape transition temperature, wherein the shape-memory Nitinol retracts to its preshape and causes the expandable tubular stent to collapse when said shape-memory Nitinol is heated to above the shape transition temperature at the retracted state. The first construction material makes up the exterior portion of the expandable tubular stent and the second construction material makes up the interior luminal portion, wherein the exterior portion and the interior luminal portion of the expandable tubular stent are secured together. The shape transition temperature for the shape-memory Nitinol is preferably between 43° C. and 90° C.

The method and the retractable intraluminal medical devices of the present invention have several significant advantages over other known systems to treat the intraluminal tissues. In particular, the retractable intraluminal medical device is retractable when a stent is required to be removed from a patent.

BRIEF DESCRIPTION OF THE DRAWINGS

Additional objects and features of the present invention will become more apparent and the invention itself will be best understood from the following Detailed Description of Exemplary Embodiments, when read with reference to the accompanying drawings.

DETAILED DESCRIPTION OF EXEMPLARY EMBODIMENTS

Referring to FIGS. 1 to 5, what is shown is an embodiment of a retractable expandable stent and methods thereof.

Figure 1:
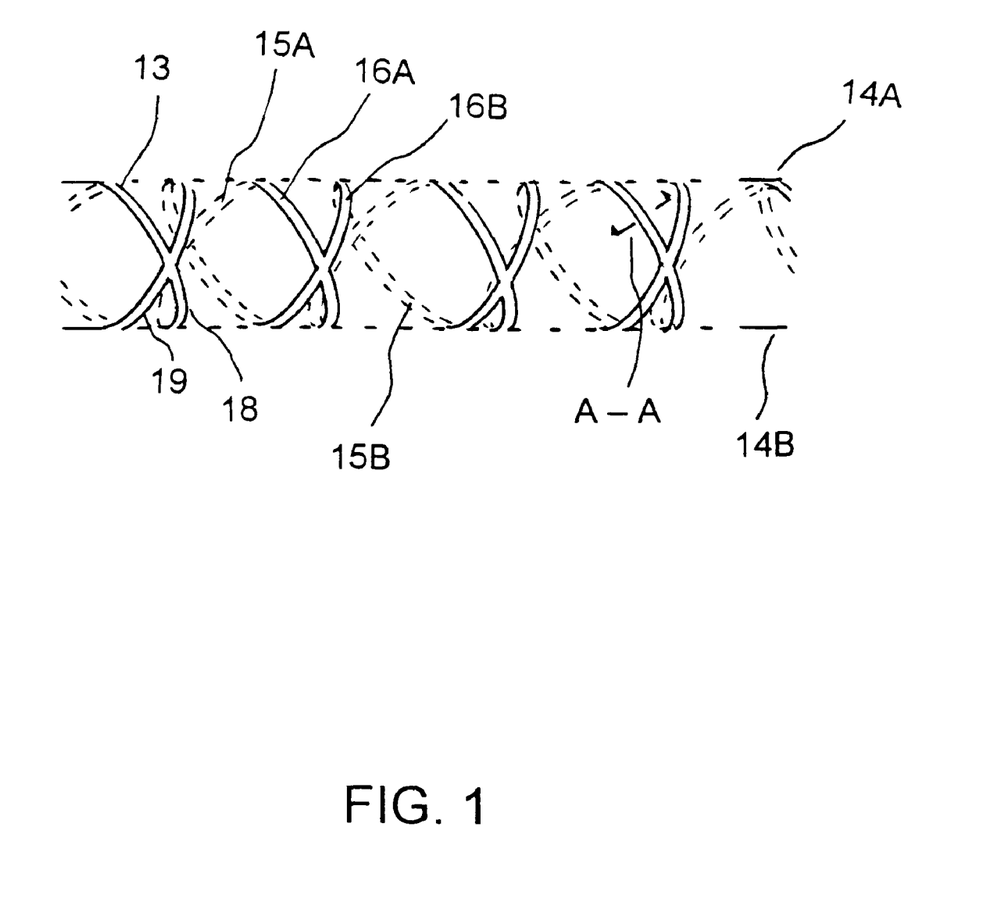
FIG. 1 is a sectional view of a preferred elongate radially expandable tubular stent having a retractable capability at a non-deployed state, constructed in accordance to the principles of the present invention.

FIG. 1 shows a section of an overall view of a preferred elongate radially expandable tubular stent 13 having a retraction or collapsing capability at a non-deployed state, constructed in accordance to the principles of the present invention. As shown in FIG. 1, the stent 13 has its radially outer boundaries 14A, 14B at a non-deployed state. These outer boundaries 14A, 14B at a non-deployed state is smaller than the radially boundaries 24A, 24B at a deployed state. When the stent 13 is to be collapsed, the outer boundaries at a collapsed/retracted state is smaller than the boundaries 24A, 24B so that the stent can be retracted from a patient. The interior luminal portion 15, 15A, 15B is to contact a body fluid, such as blood in a vascular stenting procedure, while the exterior portion 16, 16A, 16B is to contact tissue when the stent 13 is deployed to support and enlarge the biological vessel or duct.

In an alternate embodiment, a mesh stent consisting of two coil wires 18, 19 in an opposite direction, which are secured together is used to lock-in and/or maintain the stent 13 at its expanded state when a stent is deployed. Said coil wires for locking-in purposes may be made of a Nitinol, other high strength material, or a composite material. For instance, one wire 18 may be made of shape-memory Nitinol of the present invention, while the other wire 19 is made of other high strength material.

Figure 2:
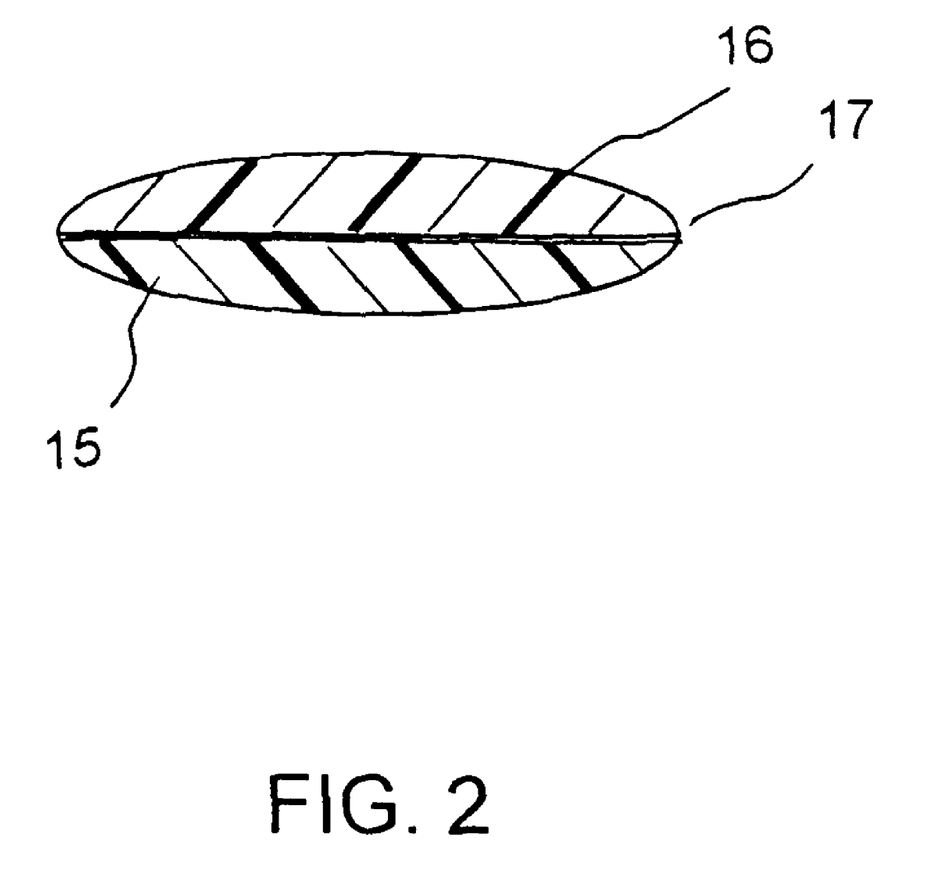
FIG. 2 is a cross-sectional view of section A—A of FIG. 1, showing an example of the two construction materials for the retractable stent.

FIG. 2 shows a cross-sectional view of section A—A of FIG. 1, showing an example of the two construction materials for the retractable stent. In a preferred embodiment, a first of the plurality of construction materials is a shape-memory Nitinol. The shape-memory Nitinol has a preshape and a shape transition temperature, wherein the shape-memory Nitinol retracts or collapses to its preshape and causes the expandable tubular stent to collapse when said shape-memory Nitinol is heated to above the shape transition temperature at the retracted state. The process 41 for making an expandable stent retractable comprises an outer portion 16 of the stent wire as shown in FIG. 2 made of shape-memory Nitinol while the inner luminal portion 15 of the stent is made of another material. A Nitinol device is well known to have a preshape and a transition temperature for said Nitinol device to reverse to its preshape.

One method for treating an intraluminal tissue of a patient may comprise collapsing the radially expanded tubular stent by heating the shape-memory Nitinol to a temperature above its shape transition temperature. Said operation for collapsing a radially expandable tubular stent may be accomplished by supplying RF energy to the stent to raise the temperature of the tissue and in turn, the tissue reflects the heat to the stent that contacts the tissue. In another preferred embodiment, the first construction material of shape-memory Nitinol makes up the exterior portion 16 of the expandable tubular stent and the second construction material makes up the interior luminal portion 15, wherein the exterior portion 16 and the interior luminal portion 15 of the expandable tubular stent are secured together at their interfaces 17. The securing methods may include bonding, welding, soldering, and the like.

Figure 3:
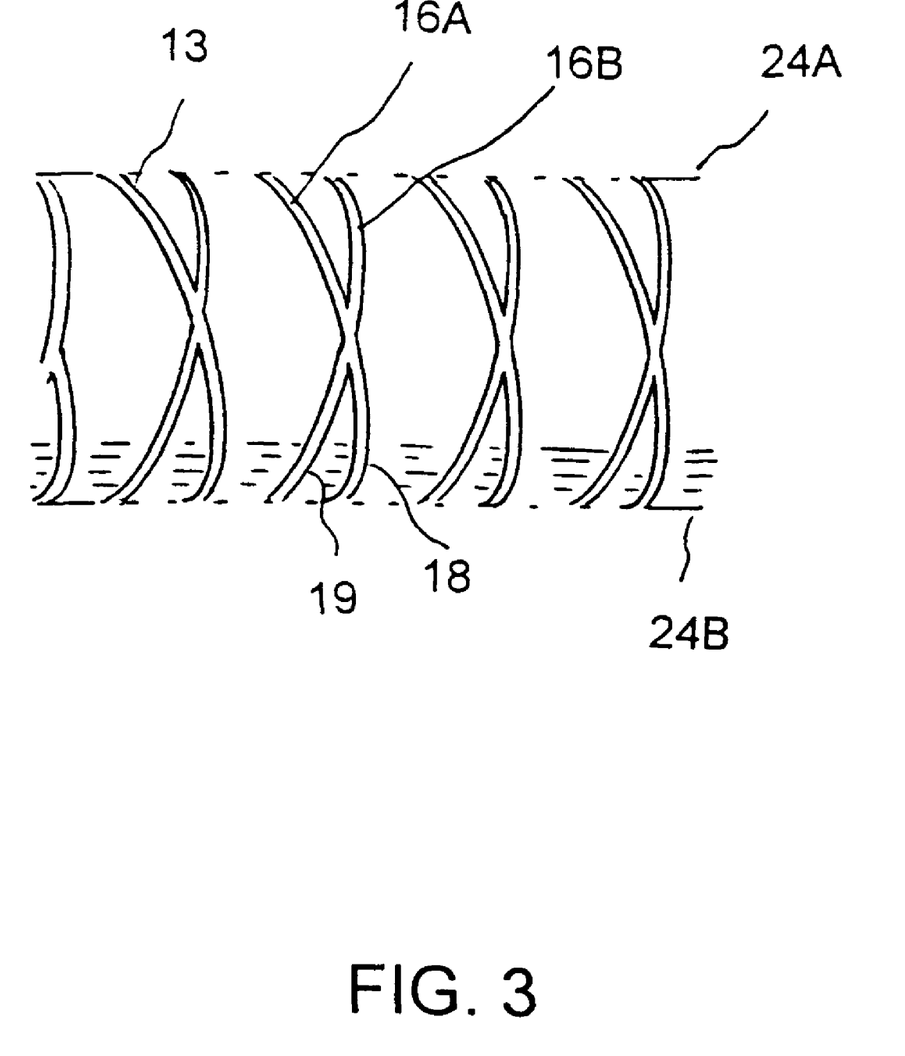
FIG. 3 is an exterior sectional view of a preferred elongate radially expandable tubular stent having a retractable capability at a deployed state, constructed in accordance to the principles of the present invention.

FIG. 3 shows an exterior sectional view of a preferred elongate radially expandable tubular stent having a retractable capability at a deployed state, constructed in accordance to the principles of the present invention. As shown in FIG. 3, the stent 13 has its radially outer boundaries 24A, 24B at a deployed state. The exterior surface 16A, 16B is to contact tissue when the stent 13 is deployed to support and enlarge the biological vessel.

The deployment of a stent can be accomplished by a balloon on a delivery catheter or by self-expanding after a pre-stressed stent is released from a delivery catheter. A delivery catheter for stent deployment and mechanisms of stent deployment are well known to one who is skilled in the art. The expandable stent 13 may be a self-expandable stent, a balloon-expandable stent or an expandable-retractable stent. The expandable stent may be made of a memory coil, mesh material, and the like.

Figure 4:
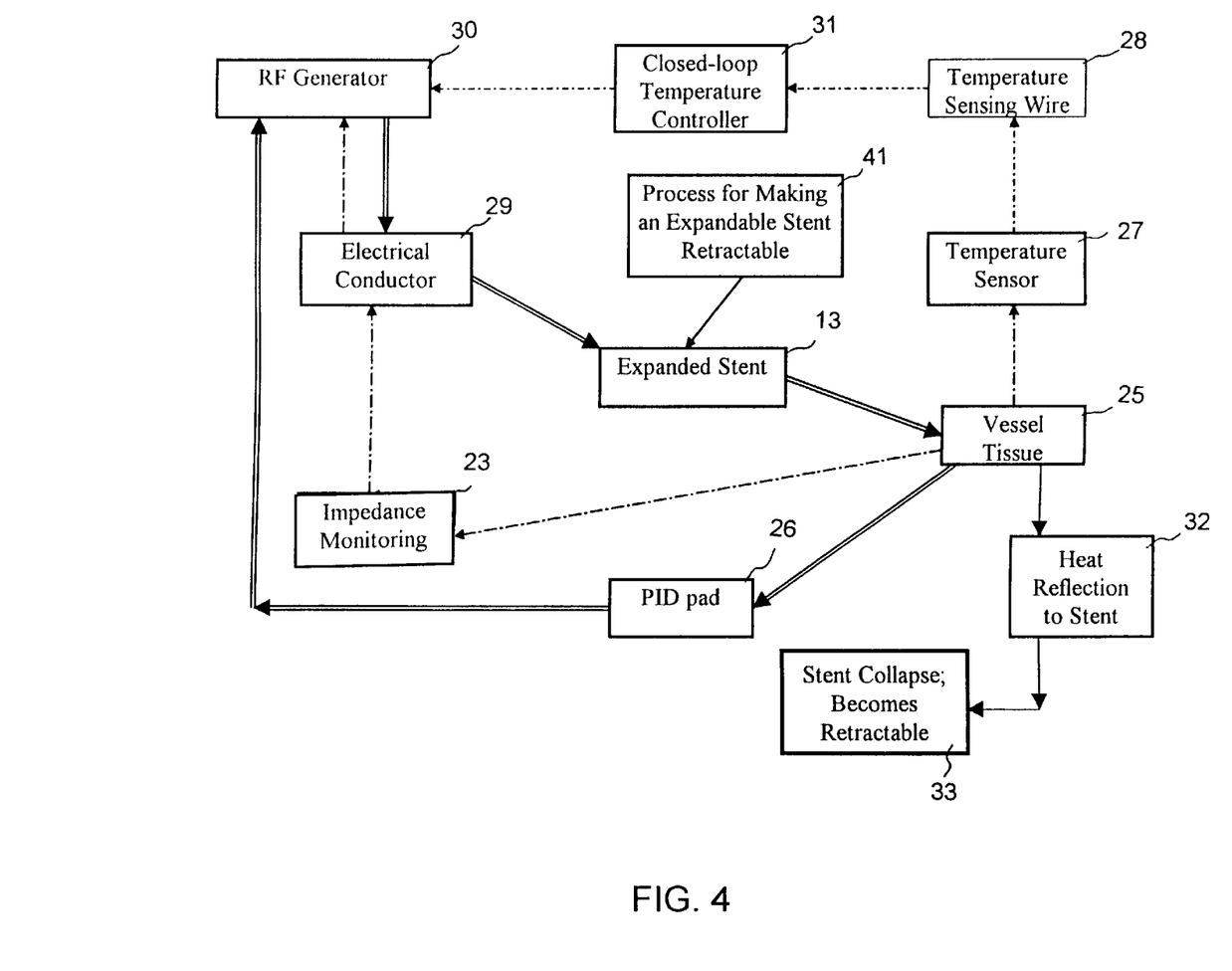
FIG. 4 is a schematic diagram of a RF generating means for causing the retractable radially expandable tubular stent to collapse.

In one embodiment, at least one temperature sensor 27 is disposed at close proximity of the expandable stent 13. Insulated temperature sensor wire means 28 passes from the temperature sensor 27, to an external temperature control mechanism 31 that is connected to a RF generator 30. The RF energy delivery is controlled by using the measured temperature from the at least one temperature sensing means 27, through a closed-loop temperature control mechanism and/or algorithm. When the measured temperature rises to a preset high-limit point (the shape transition temperature), the temperature control mechanism sends out a signal to cut off the RF energy supply. At this moment, the shape-memory Nitinol is already collapsed because the temperature of the Nitinol exceeds the shape transition temperature.

FIG. 4 shows a schematic diagram of a RF generating means for causing the retractable radially expandable tubular stent to collapse. A RF generator 30 is connected to an expanded stent 13 through an electrical conductor 29. In one embodiment, the stent 13 is to contact the underlying tissue 25 at a stent deployed state. A DIP (dispersive indifferent pad) type pad 26, that contacts a patient, is connected to the Indifferent Electrode Connector on the RF generator 30. Therefore, the RF energy delivery becomes effective when a close circuit from a RF generator 30 through a stent, a patient and returning to the RF generator is formed. Impedance 23 measured from the tissue contact is to ensure good tissue contact for RF energy delivery through the stent 13, otherwise the RF power is cutoff when the impedance is unreasonably beyond the acceptance range. A temperature sensor 27 may also used to measure the tissue temperature and is relayed through a temperature sensing wire 28 and a closed-loop temperature controller 31 for controlling the RF energy delivered. Heat to the tissue is controlled by the power of the RF energy delivered and by the delivery duration. The heat 32 reflects back to the stent and causes the stent to collapse 33 when a stent needs to be retracted.

Figure 5:
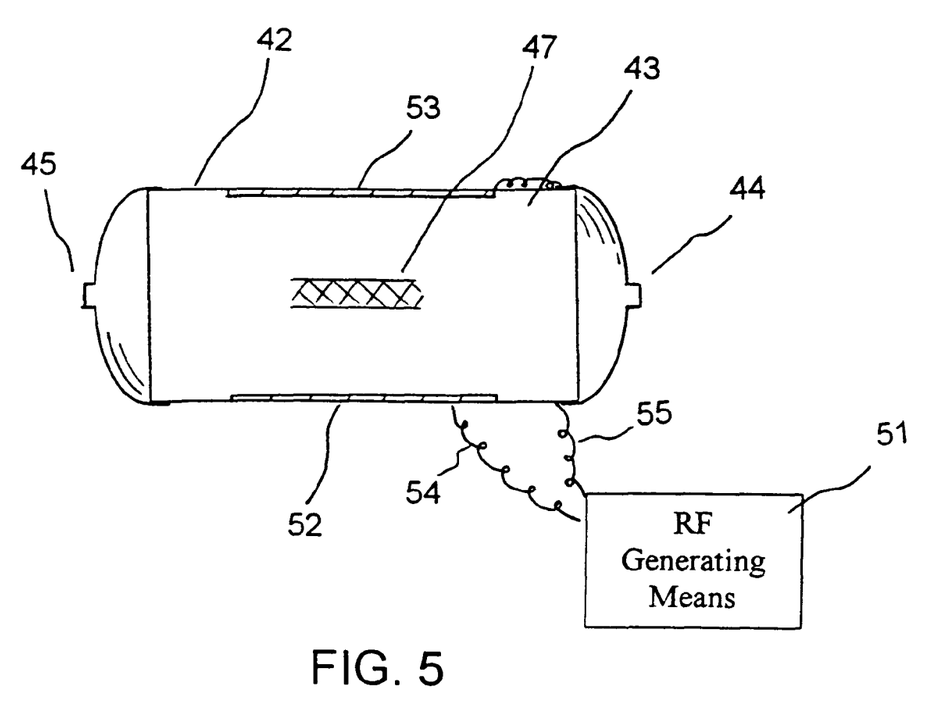
FIG. 5 is a diagram of a preferred fluorination process for making a fluorinated retractable stent via glow discharge method.

The retractable intraluminal medical device may comprise the fluorine-containing coating to render the surface more biocompatible, wherein the coating is selected from a group consisting of glow discharge coating, adhesive coating, impregnating coating, compound coating, dip coating, paste coating, and sintering. FIG. 5 shows a diagram of a preferred fluorination process for making a fluorinated stent via glow discharge method. A fluorination reaction vessel 42 comprises a vacuum chamber 43, a gas inlet port 44, a gas outlet port 45, the device 47 (e.g. a stent 13) to be fluorinated, and a radiofrequency generating means 51 having a bipolar electrode setup 52, 53 and its associated conducting wires 54, 55 to create a RF field for glow discharging fluorine-containing plasma onto the surface of said device 47. The fluorination process via glow discharge method is well known to one who is skilled in the art. The major parameters for operation include the radiofrequency power level, the fluorine-containing gas used, the concentration of the gas, the degree of vacuum prior to gas introduction, and the configuration of the device to be fluorinated.

A method for treating an intraluminal tissue of a patient, the method comprises the steps of (a) positioning an intraluminal medical device at an appropriate intraluminal tissue site, the intraluminal medical device comprising an elongate radially expandable tubular stent having an interior luminal portion and an opposite exterior portion extending along a longitudinal stent axis, the elongate radially expandable tubular stent having an expanded state and a retracted state, wherein the expandable tubular stent comprises a plurality of construction materials; and a first of the plurality of construction materials being a shape-memory Nitinol, the shape-memory Nitinol having a preshape and a shape transition temperature, wherein the shape-memory Nitinol retracts to its preshape and causes the expandable tubular stent to collapse when said shape-memory Nitinol is heated to above the shape transition temperature at the retracted state; and (b) deploying the radially expandable tubular stent.

The method for treating an intraluminal tissue of a patient further comprises collapsing the radially expanded tubular stent by heating the shape-memory Nitinol to a temperature above its shape transition temperature. The radially expandable tubular stent may be deployed by releasing said stent from a distal end of a delivery catheter. The radially expandable tubular stent may also be deployed by an inflatable balloon on a catheter.

The method for treating an intraluminal tissue of a patient further comprises applying RF current to the expandable tubular stent to effect collapsing of the radially expandable tubular stent, wherein the retractable intraluminal medical device further comprises RF current generating means for generating RF current, wherein the RF current generating means is connected to the radially expandable tubular stent and is adapted for delivering RF current to the radially expandable tubular stent. The method may further comprise measuring temperature, wherein the retractable intraluminal medical device further comprises temperature sensing means positioned at close proximity of the exterior portion of the expandable tubular stent, and wherein said temperature sensing means comprises a thermocouple or a thermister measuring probe. The method may further comprise relaying measured temperature from the temperature sensing means to a temperature control means, wherein the temperature sensed is adapted to effect the RF current delivery to the expandable tubular stent.

The elongate radially expandable tubular stent may be selected from a group consisting of a vascular stent, a grafted stent, a coil stent, a mesh stent, a scaffold stent, a sleeve stent, a porous stent made of porous material, and a permeable stent.

The external RF current generator means has the capability to supply RF current by controlling the time, power, and temperature through an optional separate closed-loop temperature control means. The patient is connected to the RF generator means through a DIP electrode to form a closed-loop RF current system. Therefore, RF energy is applied and delivered to the targeted tissue region, through the expandable stent or metallic member of this invention. The radiofrequency energy current in this invention is preferably within the range of 50 to 2,000 kHz.

In a particular embodiment, the stent for the RF current delivery of this invention consists of conductive metals such as platinum, iridium, gold, silver, stainless steel, Nitinol, or an alloy of these metals. The elongate radially expandable tubular stent in this invention is selected from group consisting of a grafted stent, a coil stent, a mesh stent, a scaffold stent, a sleeve stent, a porous stent, and a permeable stent.

From the foregoing description, it should now be appreciated that a retractable radially expandable tubular stent has been disclosed. While the invention has been described with reference to a specific embodiment, the description is illustrative of the invention and is not to be construed as limiting the invention. Various modifications and applications may occur to those who are skilled in the art, without departing from the true spirit and scope of the invention, as described by the appended claims.

What is claimed is:

1. A retractable intraluminal medical device comprising:
   an elongate radially expandable tubular stent having an interior luminal portion and an opposite exterior portion extending along a longitudinal stent axis, the elongate radially expandable tubular stent having an expanded state and a retracted state, wherein the expandable tubular stent comprises a plurality of construction materials; and
   a first of the plurality of construction materials being a shape-memory Nitinol, the shape-memory Nitinol having a preshape and a shape transition temperature, wherein the shape-memory Nitinol retracts to its preshape and causes the expandable tubular stent to collapse when said shape-memory Nitinol is heated to above the shape transition temperature at the retracted state, and wherein the shape transition temperature for the shape-memory Nitinol is preferably between 43° C. and 90° C.

2. The retractable intraluminal medical device of claim 1, wherein surface of the expandable tubular stent is coated with fluorine-containing compound, and wherein the surface is selected from a group consisting of a surface of the interior luminal portion, a surface of the opposite exterior portion, or an entire surface of the expandable tubular stent.

3. The retractable intraluminal medical device of claim 1, wherein a second of the plurality of construction materials is selected from a group consisting of stainless steel, gold, silver, copper, Nitinol, platinum, and an alloy of the mixtures.

4. The retractable intraluminal medical device of claim 1, wherein the elongate radially expandable tubular stent is selected from a group consisting of a vascular stent, a grafted stent, a coil stent, a mesh stent, a scaffold stent, a sleeve stent, a porous stent made of porous material, and a permeable stent.

5. The retractable intraluminal medical device of claim 1, wherein the expandable tubular stent comprises an appropriate quantity of the first of the plurality of construction materials adapted to cause the expandable tubular stent to collapse when the stent is at the retracted state.

6. The retractable intraluminal medical device as in claim 1 further comprising RF current generating means for generating RF current, wherein the RF current generating means is connected to the radially expandable tubular stent, is adapted for delivering RF current to the radially expandable tubular stent and causes the radially expandable tubular stent to collapse.

7. The retractable intraluminal medical device as in claim 6 further comprising temperature sensing means positioned at close proximity of the exterior portion of the expandable tubular stent for measuring temperature, wherein said temperature sensing means comprises a thermocouple or a thermister measuring probe.

8. The retractable intraluminal medical device as in claim 7 further comprising temperature control means for receiving temperature readings, wherein the temperature readings sensed from the temperature sensing means is relayed to the temperature control means and is adapted to effect the RF current delivery to the expandable tubular stent.

9. The retractable intraluminal medical device of claim 6, wherein the RF current is within the range of 50 to 2,000 kHz.

10. A method for treating an intraluminal tissue of a patient, the method comprising the steps of:
   (a) positioning a retractable intraluminal medical device at an appropriate intraluminal tissue site, the retractable intraluminal medical device comprising an elongate radially expandable tubular stent having an interior luminal portion and an opposite exterior portion extending along a longitudinal stent axis, the elongate radially expandable tubular stent having an expanded state and a retracted state, wherein the expandable tubular stent comprises a plurality of construction materials; and a first of the plurality of construction materials being a shape-memory Nitinol, the shape-memory Nitinol having a preshape and a shape transition temperature, wherein the shape-memory Nitinol retracts to its preshape and causes the expandable tubular stent to collapse when said shape-memory Nitinol is heated to above the shape transition temperature at the retracted state, and wherein the shape transition temperature for the shape-memory Nitinol is preferably between 43° C. and 90° C.;
   (b) deploying the radially expandable tubular stent.

11. The method for treating an intraluminal tissue of a patient as in claim 10, the method further comprising collapsing the radially expanded tubular stent by heating the shape-memory Nitinol to a temperature above its shape transition temperature.

12. The method for treating an intraluminal tissue of a patient as in claim 10, wherein the radially expandable tubular stent is deployed by releasing said stent from a distal end of a delivery catheter.

13. The method for treating an intraluminal tissue of a patient as in claim 10, wherein the radially expandable tubular stent is deployed by an inflatable balloon on a catheter.

14. The method for treating an intraluminal tissue of a patient as in claim 11, wherein the method further comprising applying RF current to the expandable tubular stent to effect collapsing of the radially expandable tubular stent, wherein the retractable intraluminal medical device further comprises RF current generating means for generating RF current, wherein the RF current generating means is connected to the radially expandable tubular stent and is adapted for delivering RF current to the radially expandable tubular stent.

15. The method for treating an intraluminal tissue of a patient as in claim 14, the method further comprising measuring temperature, wherein the retractable intraluminal medical device further comprises temperature sensing means positioned at close proximity of the exterior portion of the expandable tubular stent, and wherein said temperature sensing means comprises a thermocouple or a thermister measuring probe.

16. The method for treating an intraluminal tissue of a patient as in claim 15, the method further comprising relaying measured temperature from the temperature sensing means to a temperature control means, wherein the temperature sensed is adapted to effect the RF current delivery to the expandable tubular stent.

17. The method for treating an intraluminal tissue of a patient as in claim 10, wherein the elongate radially expandable tubular stent is selected from a group consisting of a vascular stent, a grafted stent, a coil stent, a mesh stent, a scaffold stent, a sleeve stent, a porous stent made of porous material, and a permeable stent.

18. A retractable intraluminal medical device comprising:

an elongate radially expandable tubular stent having an interior luminal portion and an opposite exterior portion extending along a longitudinal stent axis, the elongate radially expandable tubular stent having an expanded state and a retracted state, wherein the expandable tubular stent comprises a first construction material and a second construction material;

the first construction material being a shape-memory Nitinol, the shape-memory Nitinol having a preshape and a shape transition temperature, wherein the shape-memory Nitinol retracts to its preshape and causes the expandable tubular stent to collapse when said shape-memory Nitinol is heated to above the shape transition temperature at the retracted state, wherein the shape transition temperature for the shape-memory Nitinol is preferably between 43° C. and 90° C.; and the first construction material making up the exterior portion of the expandable tubular stent and the second construction material making up the interior luminal portion, wherein the exterior portion and the interior luminal portion of the expandable tubular stent are secured together.

* * * * *